(12) United States Patent
Kellner et al.

(10) Patent No.: US 7,052,514 B2
(45) Date of Patent: May 30, 2006

(54) METHODS AND REAGENTS FOR TISSUE ENGINEERING OF CARTILAGE IN VITRO

(75) Inventors: Karin Kellner, Regensburg (DE); Kurt Lang, Penzberg (DE); Apollon Papadimitriou, Bichl (DE); Ulrike Leser-Reiff, Munich (DE); Michaela Schultz, Regensburg (DE); Torsten Blunk, Pentlingg (DE); Achim Goepferich, Sinzing (DE)

(73) Assignee: Curis, Inc., Cambridge, MA (US)

( * ) Notice: Subject to any disclaimer, the term of this patent is extended or adjusted under 35 U.S.C. 154(b) by 610 days.

(21) Appl. No.: 09/844,257

(22) Filed: Apr. 27, 2001

(65) Prior Publication Data

US 2002/0015719 A1 Feb. 7, 2002

Related U.S. Application Data

(60) Provisional application No. 60/200,767, filed on Apr. 28, 2000.

(51) Int. Cl.
*A61F 3/00* (2006.01)
*A61F 5/00* (2006.01)
*G01N 33/567* (2006.01)

(52) U.S. Cl. ............ 623/11.11; 623/13.11; 623/17.15; 514/2; 424/523; 427/2.26; 530/350; 530/399; 530/402

(58) Field of Classification Search ............... 435/6, 435/7, 21, 69.1, 252.1, 1.1, 283.1; 424/93.7; 514/2; 436/501; 623/13.11, 128, 898
See application file for complete search history.

(56) References Cited

U.S. PATENT DOCUMENTS

| | | | |
|---|---|---|---|
| 4,642,120 A | 2/1987 | Nevo et al. | |
| 4,846,835 A | 7/1989 | Grande | |
| 4,904,259 A | 2/1990 | Itay | |
| 5,041,138 A | 8/1991 | Vacanti et al. | |
| 5,053,050 A | 10/1991 | Itay | |
| 5,206,023 A | 4/1993 | Hunziker | |
| 5,270,300 A | 12/1993 | Hunziker | |
| 5,844,079 A * | 12/1998 | Ingham et al. | ............... 530/350 |
| 5,972,385 A | 10/1999 | Liu et al. | |
| 6,444,793 B1 * | 9/2002 | Pepinsky et al. | ............ 530/402 |
| 6,468,978 B1 * | 10/2002 | Esswein et al. | ................ 514/21 |

FOREIGN PATENT DOCUMENTS

| | | |
|---|---|---|
| EP | 0978285 | 8/1999 |
| WO | WO 95/33821 | 12/1995 |

OTHER PUBLICATIONS

Stull and Iacovitti, Experimental Neurobiology 169(1)36-43, 2001.*
Marti, S. et al., Nature 375(322-325)1995.*
Bowie et al., 1990, Science 247:1306-1310.*
Seytter-T et al., Abstract No. A151, p. S563, JBMR ,Nov. 1998.*
Aston, Jayne E. & Bentley, George. Repair of articular surfaces by allografts of articular and growth-plate cartilage. *J. Bone Joint Surg.* 68B:29-35 (1986).
Bentley et al. Homotransplantation of isolated epiphyseal and articular cartilage chondrocytes into joint surfaces of rabbits. *Nature* 230:385-388 (1971).
Freed, Lisa E. et al. Neocartilage formation *in vitro* and *in vivo* using cells cultured on synthetic biodegradable polymers. *J. of Biomedical Materials Research* 27, 11-23 (1993).
Freed, Lisa E. & Vunjak-Novakovic, Gordana. Tissue Engineering of Cartilage. *The Biomedical Engineering Handbook, CRC Press* 1788-1806 (1995).
Gooch, K. et al. in *Frontiers of Tissue Engineering, Pergamon*, 68-73 (1998).
Grande, David A. et al. The Repair of Experimentally Produced Defects in Rabbit Articular Cartilage by Autologous Chondrocyte Transplantation. *J. Orthop. Research* 7:208-218 (1989).
Green, William T. Jr. Articular Cartilage Repair: Behavior of rabbit chondrocytes during tissue culture and subsequent allografting. *Clinical Orthop. and Related Research* 124:237-250 (1977).
Iwanoto, M. et al. Actions of Hedgehog Proteins on Skeletal Cells. *Crit. Rev. Oral Biol. Med.* 10(4):477-486 (1999).

(Continued)

*Primary Examiner*—Elizabeth Kemmerer
*Assistant Examiner*—Michael Brannock
(74) *Attorney, Agent, or Firm*—Fish & Neave IP Group Ropes & Gray LLP

(57) ABSTRACT

The present invention makes available an optimal concentration of a hedgehog polypeptide for modulating growth and/or cartilage production by chondrocytes. The present invention allows for improvements in the culturing of chondrocytes to develop cartilaginous tissue ex vivo suitable for implantation to replace damaged or deteriorated cartilage in a patient.

6 Claims, 3 Drawing Sheets

OTHER PUBLICATIONS

Iwasaki, M., Jikko, A. & Le, a. X. Age-dependent effects of hedgehog protein on chondrocytes. *J. Bone Joint Surg.* 81,1076-1082 (1999).

Kronenberg, H. M. et al. Parathyoid hormone-related protein and Indian hedgehog control the pace of cartilage differentiation. *J. Endrocrinology* 154:39-45 (1997).

Langer, Fred. et al. Immunogenicity of allograft articular cartilage. *J. Bone Joint Surg.* 56A:297-304 (1974).

Nixon, Alan J. et al. Temporal matrix synthesis and histologic features of a chondrocyte-laden porous collagen cartilage analogue. *Am. J. Vet. Res.* vol. 54, No. 2, 349-356 (Feb. 1993).

Pepinsky, R. Blake et al. Identification of a palmitic acid-modified form of human sonic hedgehog. *J. Biol. Chem.* 273:14037-14045 (1998).

Robinson, Dror et al. Regenerating hyaline cartilage in articular defects of old chickens using implants of embryonal chick chondrocytes embedded in a new natural delivery substance. *Calcified Tissue International* 46:246-253 (1990).

Stone, Kevin R. et al. Future Directions: Collagen-based prostheses for meniscal regeneration. *Clinical Orthop. and Related Research* 252:129135 (1990).

Takigawa, Masaharu et al. Chondrocytes dedifferentiated by serial monolayer culture from cartilage nodules in nude mice. *Bone and Mineral* 2:449-462 (1987).

Vacanti, C. A. et al. Synthetic polymers seeded with chondrocytes provide a template for new cartilage formation. *Plastic and Reconstructive Surg.* 88:753-759 (1991).

von Schroeder, Herbert P. et al. The use of polylactic acid matrix and periosteal grafts for the reconstruction of rabbit knee articular defects. *J. Biomed. Mat. Research* 25:329-339 (1991).

Vortkamp, Andrea et al. Recapitulation of signals regulating embryonic bone formation during postnatal growth and in fracture repair. *Mech. Development* 71, 65-76 (1998).

Wakitani, Shigeyuki et al. Repair of rabbit articular surfaces with allograft chondrocytes embedded in collagen gel. *J. Bone Joint Surg.* 71B:74-80 (1989).

Yasui, Natsuo et al. Repair of rabbit articular surfaces with allograft chondrocytes embedded in collagen gels. *J. Jpn. Ortho. Assoc.* 63, 529-538 (1989).

* cited by examiner

METHODS AND REAGENTS FOR TISSUE ENGINEERING OF CARTILAGE IN VITRO

This application claims priority to U.S. provisional application 60/200,767, filed Apr. 28, 2000, the disclosure of which is hereby incorporated by reference in its entirety.

BACKGROUND OF THE INVENTION

Cartilage is a structural tissue constructed from a variety of hydrated biopolymers. By weight, water comprises 70% to 80% of cartilage. The remaining 20% to 30% comprises extracellular biopolymers such as collagen (primarily type-II) and proteoglycan. The collagen usually accounts for 70% of the dry weight of cartilage (in "Pathology" (1988) Eds. Rubin & Farber, J. B. Lippincott Company, PA. pp. 1369–1371). Proteoglycans are composed of a central protein core from which long chains of polysaccharides extend. These polysaccharides, called glycosaminoglycans, include: chondroitin-4-sulfate; chondroitin-6-sulfate; and keratan sulfate. Chondrocytes are cells responsible for the ordered production and secretion of the cartilagenous polymers. The properties of cartilage are primarily determined by the quantity and quality of the extracellular biopolymers.

Three types of cartilage are present in mammals and include: hyaline cartilage, fibrocartilage, and elastic cartilage (Rubin and Farber, supra). Hyaline cartilage consists of a gristly mass having a firm, elastic consistency, is translucent and is pearly blue in color. Hyaline cartilage is predominantly found on the articulating surfaces of articulating joints. It is found also in epiphyseal plates, costal cartilage, tracheal cartilage, bronchial cartilage and nasal cartilage. Fibrocartilage is essentially the same as hyaline cartilage except that it contains fibrils of type I collagen that add tensile strength to the cartilage. The collagenous fibers are arranged in bundles, with the cartilage cells located between the bundles. Fibrocartilage is found commonly in the anulus fibrosus of the invertebral disc, tendinous and ligamentous insertions, menisci, the symphysis pubis, and insertions of joint capsules. Elastic cartilage also is similar to hyaline cartilage except that it contains fibers of elastin. It is more opaque than hyaline cartilage and is more flexible and pliant. These characteristics are defined in part by the elastic fibers embedded in the cartilage matrix. Typically, elastic cartilage is present in the pinna of the ears, the epiglottis, and the larynx.

The surfaces of articulating bones in mammalian joints are covered with articular cartilage. The articular cartilage prevents direct contact of the opposing bone surfaces and permits the near frictionless movement of the articulating bones relative to one another (Clemente, supra).

Two types of articular cartilage defects are commonly observed in mammals and include full-thickness and partial-thickness defects. The two types of defects differ not only in the extent of physical damage but also in the nature of repair response each type of lesion elicits.

Full-thickness articular cartilage defects include damage to the articular cartilage, the underlying subchondral bone tissue, and the calcified layer of cartilage located between the articular cartilage and the subchondral bone. Full-thickness defects typically arise during severe trauma of the joint or during the late stages of degenerative joint diseases, for example, during osteoarthritis. Since the subchondral bone tissue is both innervated and vascularized, damage to this tissue is often painful. The repair reaction induced by damage to the subchondral bone usually results in the formation of fibrocartilage at the site of the full-thickness defect. Fibrocartilage, however, lacks the biomechanical properties of articular cartilage and fails to persist in the joint on a long term basis.

Partial-thickness articular cartilage defects are restricted to the cartilage tissue itself. These defects usually include fissures or clefts in the articulating surface of the cartilage. Partial-thickness defects are caused by mechanical arrangements of the joint which in turn induce wearing of the cartilage tissue within the joint. In the absence of innervation and vasculature, partial-thickness defects do not elicit repair responses and therefore tend not to heal. Although painless, partial-thickness defects often degenerate into full-thickness defects.

Repair of articular cartilage defects with suspensions of isolated chondrocytes has been attempted in a variety of animal models. See for example: Bentley, et al. (1971) Nature 230:385–388; Langer et al. (1974) J. Bone Joint Surg. 56A:297–304; Green (1977) Clin. Orthop. 124:237–250; and Aston et al. (1986) J. Bone Joint Surg. 68B:29–35). During transplantation, the cell suspensions may be retained in the defect behind a piece of periosteal tissue that has been previously attached to the surface of the normal cartilage tissue. The rate of successful implantation using cell suspensions was found to be about 40%. It is believed that chondrocytes transplanted in this manner lose their viability during transplantation and that the procedure may result in the formation of fibrocartilage or islands of cartilage embedded in fibrous tissue at the site of the defect.

Three alternative approaches have been developed in an attempt to improve the success rate in treating mammalian articular cartilage defects. In the first approach, synthetic carrier matrices containing dispersed allogeneic chondrocytes may be implanted into the cartilage defect. The implanted chondrocytes hopefully produce and secrete components of the extracellular matrix thereby to form articular cartilage at the site of the defect in situ. In the second approach, synthetic carrier matrices containing chemotactic and mitogenic growth factors may be implanted into the cartilage defect. The growth factors hopefully induce the influx into, and the proliferation of chondrocyte progenitor cells within the matrix. The chondrocyte progenitor cells differentiate subsequently into chondrocytes that in turn secrete components of the extracellular matrix thereby to form articular cartilage at the site of the defect in situ. In the third approach, synthetic cartilage tissue may be grown in vitro and implanted subsequently into the cartilage defect.

In the first approach, the synthetic matrices or biological resorbable immobilization vehicles may be impregnated with allogeneic chondrocytes. A variety of synthetic carrier matrices have been used to date and include: three-dimensional collagen gels (U.S. Pat. No. 4,846,835; Nishimoto (1990) Med. J. Kinki University 15;75–86; Nixon et al. (1993) Am. J. Vet. Res. 54:349–356; Wakitam et al. (1989) J. Bone Joint Surg. 71B:74–80; Yasui (1989) J. Jpn. Ortho. Assoc. 63:529–538); reconstituted fibrinthrombin gels (U.S. Pat. No. 4,642,120; U.S. Pat. No. 5,053,050 and U.S. Pat. No. 4,904,259); synthetic polymer matrices containing polyanhydride, polyorthoester, polyglycolic acid and copolymers thereof (U.S. Pat. No. 5,041,138); and polyanhydride, polyorthoester hyaluronic acid-based polymers (Robinson et al. (1990) Calcif. Tissue Int. 46:246–253); and glycosaminoglycans or dextran sulfate.

The introduction of non-autologous materials into a patient, however, may stimulate an undesirable immune response directed against the implanted material. Such an immune response has been observed in rabbit models (Yoshinao (1990) J. Jpn. Orth. Assoc. 64:835–846. In addition, there is evidence to suggest that neo-cartilage may be formed around the periphery of the implant thereby preventing integration of the implant into the cartilage defect. See for example, Messner (1994) 40'" Annual Meeting Orth. Res. Soc., New Orleans p. 239; and Nixon et al. (1994) 40' Annual Meeting Orth. Res. Soc., New Orleans p. 241. Monitoring the formation and development of the resulting synthetic cartilage in situ can be difficult to perform and usually involves an arthroscopic or open joint examination. Furthermore, implants containing synthetic polymer components may be unsuitable for repairing large cartilage defects since polymer hydrolysis in situ may inhibit the formation of cartilage and/or its integration into the defect.

In the second approach, the defect may be filled with a biocompatible, biodegradable matrix containing growth factors to stimulate the influx of chondrocyte progenitor cells into the matrix in situ. The matrices optimally contain pores of sufficient dimensions to permit the influx into, and proliferation of the chondrocyte progenitor within the matrix. The matrix also may contain differentiating growth factors to stimulate the differentiation of chondrocyte progenitor cells into chondrocytes. The resulting chondrocytes hopefully secrete extracellular matrix components thereby to form cartilage at the site of the defect in situ. See for example, U.S. Pat. No. 5,206,023; U.S. Pat. No. 5,270,300; and EP 05 30 804 A1. This approach, however, may have problems similar to those associated with the first approach, herein above.

In the third approach, chondrocytes may be cultured in vitro to form synthetic cartilage-like material. The resulting cartilage may be implanted into the cartilage defect. This type of approach has the advantage over the previous methods in that the development of the synthetic cartilage material may be monitored prior to implantation. In addition, the resulting cartilage may be characterized biochemically and morphologically prior to implantation.

In vitro tissue engineering of cartilage on a polymer matrix is problematic because the resultant cell-polymer construct often has properties that are unfavorable for successful grafting. Particularly, the quantity and quality of secreted polymers does not adequately mimic that found in natural cartilage. Typically the amount of proteoglycan and collagen (measured relative to cell number or to total wet weight of the cell-polymer construct) is lower than in natural cartilage.

It has previously been demonstrated that hedgehog polypeptides (including hydrophobically-modified hedgehog polypeptides) have trophic effects on chondrocytes both in vivo and in vitro. (Iwasaki, Jikko & Le, 1999, Br. J Bone Joint Sur. 81, 1076; Iwanoto, et al., 1999, Crit Rev. Oral Biol. Med. 10, 477–86.). U.S. Pat. No. 5,972,385 suggests, but does not exemplify, the use of a oxidized polysaccharide matrix for the induction of connective tissue, including cartilage, which matrix is loaded with collagen and may be optionally loaded with a growth factor such as a hedgehog protein by co-valent linkage. The reference patent does not suggest for which type of connective tissue the use of a hedgehog protein is appropriate.

It would be advantageous to identify whether and in what optimal amounts of hedgehog polypeptides can be used to produce in vitro by culturing of chondrocytes in vitro a cartilage better adapted for implantation.

SUMMARY OF THE INVENTION

In-vitro tissue engineering of cartilage using biodegradable three-dimensional polymer meshes is one approach to solve the medical problems associated with defective cartilage due to trauma, congenital abnormalities or arthritis (Freed, L E, 1995, in: The Biomedical Engineering Handbook, CRC Press, 1788–1806). To improve the properties of the tissue developed in tissue engineering, the addition of exogenous growth factors can be useful (Gooch et al., 1998, Frontiers of Tissue Engineering, Pergamon 68–73).

The present invention discloses the use of a hedgehog therapeutic as a trophic factor in the tissue-culture production of cartilage for implantation. The invention further discloses the use of hydrophobically-modified hedgehog proteins for this purpose. One aspect of the present invention is the use of optimal concentrations of hydrophobically-modified hedgehog proteins in the range of about 500–1000 ng/ml of dipalmitoyl sonic hedgehog.

DETAILED DESCRIPTION OF THE INVENTION

I. Overview

Figure 1:
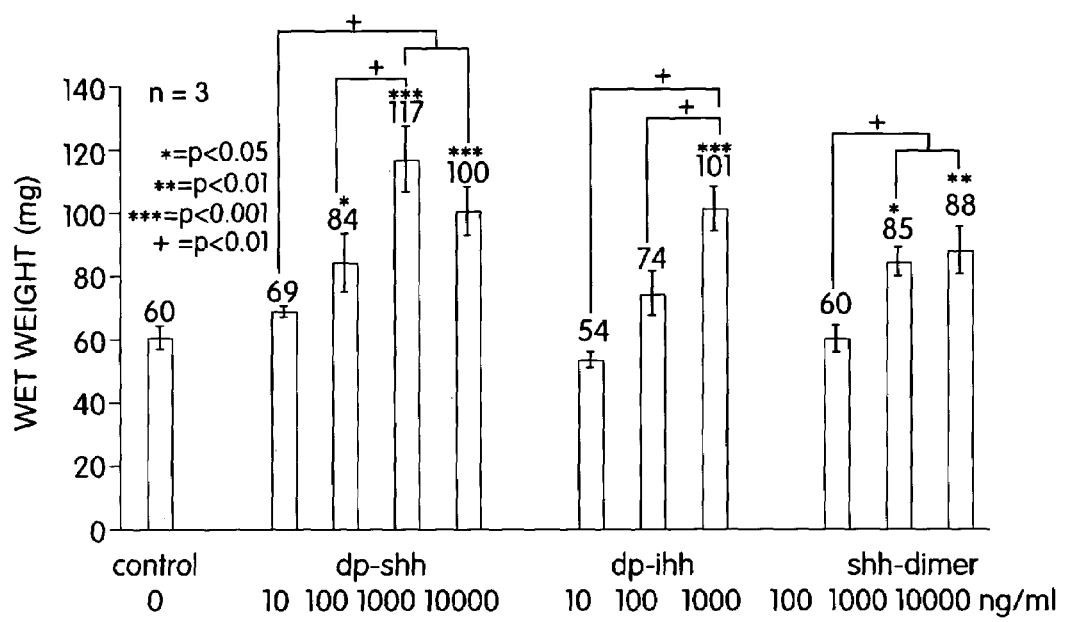
FIG. 1: Wet weight of the different cell-polymer constructs after 4 week culture.

The present invention makes available an optimal concentration of a hedgehog polypeptide for modulating growth and/or cartilage production by chondrocytes. The present invention allows for improvements in the culturing of chondrocytes to develop cartilaginous tissue ex vivo suitable for implantation to replace damaged or deteriorated cartilage in a patient.

II. Definitions

For convenience, certain terms employed in the specification, examples, and appended claims are collected here.

An "effective amount" of, e.g., a therapeutic compound, with respect to the subject method of treatment, refers to an amount of the compound in a preparation which, when applied as part of a desired dosage regimen brings about a desirable response according to clinically acceptable standards for the disorder to be treated.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hedgehog therapeutic" refers to various forms of hedgehog polypeptides, as well as peptidomimetics, which can modulate the proliferation/differentiation state of chondrocytes directly or indirectly. For instance, the hedgehog therapeutic may interact chondrocytes or progenitors thereof to effect their proliferative state. The hedgehog therapeutic may also function by inducing or inhibiting, as will be clear from the context of individual examples, expression of a parathyroid hormone-related protein. The term includes naturally occurring forms of hedgehog proteins, as well as modified or mutant forms generated by molecular biological techniques, chemical synthesis, etc. While in preferred embodiments the hedgehog polypeptide is derived from a vertebrate homolog, cross-species activity reported in the literature supports the use of hedgehog polypeptides from invertebrate organisms as well. Naturally and non-naturally occurring hedgehog therapeutics referred to herein as "agonists" mimic or potentiate (collectively "agonize") the effects of a naturally-occurring hedgehog protein on bone formation, chondrocyte proliferation, etc. In addition, the term "hedgehog therapeutic" includes molecules which can activate expression of an endogenous hedgehog gene. The term also includes gene therapy constructs for causing expression of hedgehog polypeptides in vivo, as for example, expression constructs encoding recombinant hedgehog polypeptides as well as trans-activation constructs for altering the regulatory sequences of an endogenous hedgehog gene by homologous recombination.

In particular, the term "hedgehog polypeptide" encompasses preparations of hedgehog proteins and peptidyl fragments thereof, both agonist and antagonist forms as the specific context will make clear.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be refered to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with a hedgehog sequence of the present invention.

The term "hydrophobically-modified hedgehog polypeptide" refers to any hedgehog polypeptide that is covalently attached to one or more lipophilic molecules. A standard definition of a lipophilic molecule is one with poor solubility in pure water. Examples of lipophilic molecules are given below.

A "patient" or "subject" to be treated by the subject method can mean either a human or non-human animal, such as a mammal.

As used herein, "proliferating" and "proliferation" refer to cells undergoing mitosis.

III. Exemplary Applications of Method and Compositions

The present invention makes available an optimal concentration of a hydrophobically-modified hedgehog polypeptide for promoting cartilage production in vitro. Such methods are useful in, for example, the production of three-dimensional cartilage grafts to repair defects or lesions in cartilage tissue. The defects or lesions may result from degenerative wear such as that which results in arthritis, as well as other mechanical derangements which may be caused by trauma to the tissue, such as a displacement of torn meniscus tissue, meniscectomy, a taxation of a joint by a tom ligament, malignancy of joints, bone fracture, or by hereditary disease.

The subject method can be applied to enhancing the generation of prosthetic cartilage devices. The need for improved treatment has motivated research aimed at creating new cartilage that is based on collagen-glycosaminoglycean templates (Stone et al. (1990) Clin Orthop Relat Red 252:129), isolated chondrocytes (Grande et al. (1989) J Orthop Res 7:208; and Takigawa et al. (1987) Bone Miner 2:449), and chondrocytes attached to natural or synthetic polymers (Walitani et al. (1989) J Bone Jt Surg 7113:74; Vacanti et al. (1991) Plast Reconstr Surg 88:753; von Schroeder et al. (1991) J Biomed Mater Res 25:329; Freed et al. (1993) J Biomed Mater Res 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint. In one embodiment of the subject method, chondrocytes are seeded into a polymeric matrix. The matrix may be composed of one or more of the following: polyglycolid acid, collagen, dextran sulfate, polyanhydride, polyorthoester, hyaluronic acid-based polymers, or glycosaminoglycans. The cell-polymer constructs are contacted with an optimal concentration of a hydrophobically-modified hedgehog polypeptide. The optimal concentration is preferably more than 500 ng/ml, more preferably more than 800 ng/ml, more preferably approximately 1000 ng/ml, and most preferably 1000 ng/ml. In this manner the production of secreted polymers such as proteoglycans and collagens is increased, as is the overall wet weight of the construct. Additionally, the chondrocytes become larger and there is more space between chondrocytes within the cell-polymer construct.

There area wide range of lipophilic moieties with which hedgehog polypeptides can be derivatived. The term "lipophilic group", in the context of being attached to a hedgehog polypeptide, refers to a group having high hydrocarbon content thereby giving the group high affinity to lipid phases. A lipophilic group can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include naturally-occurring and synthetic aromatic and non-aromatic moieties such as fatty acids, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

Particularly useful as lipophilic molecules are alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C 1–C 18)alkyl phosphate diesters, —O—CH2—CH(OH)—O—(C12–C18)-alkyl, and in particular conjugates with pyrene derivatives. The lipophilic moiety can be a lipophilic dye suitable for use in the invention include, but are not limited to, diphenylhexatriene, Nile Red, N-phenyl-1-naphthylamine, Prodan, Laurodan, Pyrene, Perylene, rhodamine, rhodamine B, tetramethylrhodamine, Texas Red, sulforhodamine, 1,1'-didodecyl3,3,3',3'tetramethylindocarbocyanine perchlorate, octadecyl rhodamine B and the BODIPY dyes available from Molecular Probes Inc.

Other exemplary lipophilic moietites include aliphatic carbonyl radical groups include 1- or 2-adamantylacetyl, 3-methyladamant-1-ylacetyl, 3-methyl-3-bromo-1-adamantylacetyl, 1-decalinacetyl, camphoracetyl, camphaneacetyl, noradamantylacetyl, norbomaneacetyl, bicyclo[2.2.2.]-oct-5-eneacetyl, 1-methoxybicyclo[2.2.2.]-oct-5-ene-2-carbonyl, cis-5-norbomene-endo-2,3-dicarbonyl, 5-norbomen-2-ylacetyl, (1R)-(−)-myrtentaneacetyl, 2-norbomaneacetyl, anti-3-oxo-tricyclo[2.2.1.0<2,6>]-heptane-7-carbonyl, decanoyl, dodecanoyl, dodecenoyl, tetradecadienoyl, decynoyl or dodecynoyl.

Exemplification

The invention now being generally described, it will be more readily understood by reference to the following examples which are included merely for purposes of illustration of certain aspects and embodiments of the present invention, and are not intended to limit the invention.

Effects of Hedgehog Proteins on Tissue Engineering of Cartilage In Vitro.

Materials:

Chondrocytes:

Bovine articular chondrocytes were isolated from the femoropatellar groove of 6 week-old calves. Cells were isolated and cultivated as previously described (5).

Polymer scaffolds:

The chondrocytes were cultured on PGA (polyglycolid acid) scaffolds. The scaffolds were produced at Albany International (Mansfield, Mass.) by extruding PGA into 13 um-diameter fibers and processing these into fibrous discs measuring 5 mm in diameter×2 mm in thickness (bulk density of 43 mg/cm').

Proteins:

As sonic hedgehog (shh) is found to be tethered to cell membranes for example in a form that contains a palmitoyl group (6) dipalmitylated sonic hedgehog (dp-shh), dipalmitylated indian hedgehog (dp-ihh) and sonic hedgehog dimer (shh-dimer) were used in varying concentrations supplemented to the culture medium.

Method

Cell culture:

Isolated chondrocytes were seeded onto the scaffolds in a spinner-flask for two days at 80 rpm in an incubator at 37° C., 5% C02x and 95% humidity. Each scaffold was then placed in a 6-well plate in 6 ml culture medium containing 1% FBS and put on an orbital shaker at 50 rpm. After two days the culture medium was changed and from this time point the effector molecules were added in varying concentrations with each medium change. Medium was replaced 3 times per week for up to 4 weeks.

Assessment of tissue quality:

Directly after harvesting the constructs were weighed (=wet weight) and cut in halves. One part was prepared as histological sample (safranin-O staining for proteoglycan and immunohistological collagen type II staining), the other part was used for biochemical analysis. Therefore this part was freeze-dried, digested overnight with papainase and then analyzed for cell number, content of total collagen and proteoglycan content of the cell-polymer construct (5).

Results and Discussion:

After four weeks a dose-dependent increase in wet weight (FIG. 1), tissue size and mechanical resistance (FIG. 1), tissue size and mechanical resistance was detected for all cell-polymer constructs receiving hedgehog proteins, with dip almitoyl-sonic hedgehog at c=1000 ng/ml showing the largest response.

Collagen amount generally increased proportionally with increasing construct weight. Collagen type tI as marker for differentiated chondrocytes was detected in abundance in all samples.

Figure 2:
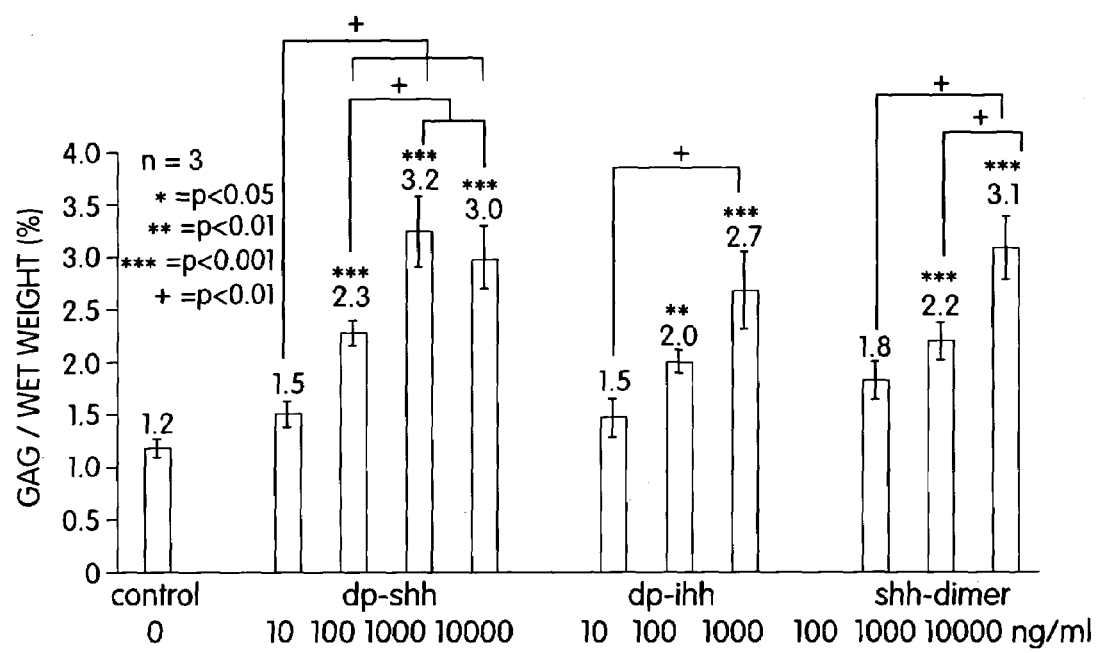
FIG. 2: Proteoglycan content per wet weight of the different cell-polymer constructs after 4 week culture.

A great concentration-dependent influence on proteoglycan content was determined for all hedgehog proteins (FIG. 2). Proteoglycan content increased to an even larger extend than the wet weight of the constructs, thus leading to an improved biochemical composition of the tissue. Dipalmityl-sonic hedgehog showed the largest effects of all at c=1000 ng/ml (2.7 fold increase compared to control constructs receiving no exogenous hedgehog protein).

Additionally the cell number per wet weight decreased with increasing hedgehog concentrations. Taken together with the increased cumulated amounts of proteoglycan and collagen the data suggested an increased ECM production for each cell.

Figure 3:
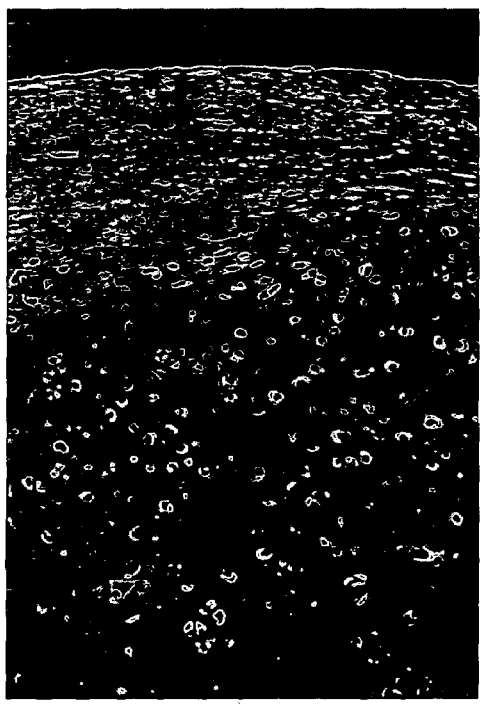
FIG. 3: Safranin O staining of grown tissue cultured without (left) and with 10000 ng/ml of hydrophobically modified sonic hedgehog protein.
Figure 3:
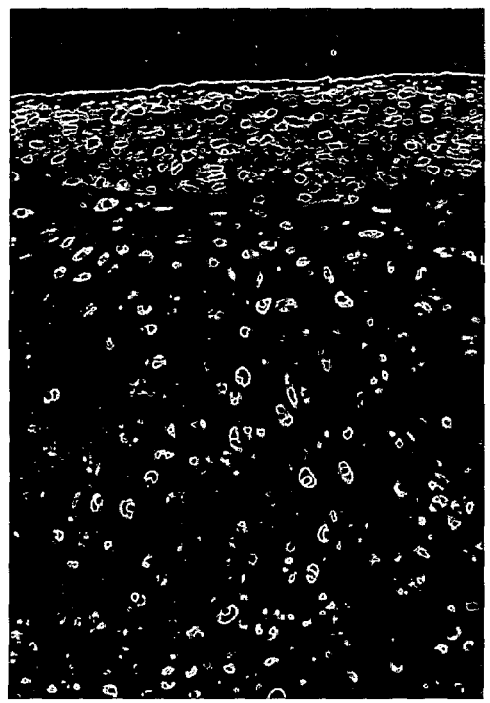

In general hedgehog proteins led to a higher proteoglycan content, a more equivalent distribution of proteoglycan and in addition a more mature tissue with bigger and a lower number of cells in the cell-polymer construct (exemplarily shown in FIG. 3).

Conclusion:

All three different modified hedgehog proteins showed a positive effect on tissueengineered cartilage, with the dipalmitylated sonic hedgehog (at c=1000 ng/ml) showing the greatest effect of all. Thus this molecule may be a candidate for use, also in combination with other growth factors, in tissue engineering of cartilage to improve the development and biochemical composition of engineered tissue.

REFERENCES (1) L. E. Freed, G. Vunjak-Novakovic, in: The Biomedical Engineering Handbook, CRC Press (1995) 1788–1806.
(2) K. Gooch, et al. In: Frontiers of Tissue Engineering, Pergamon (1998) 68–73.
(3) H. M. Kronenberg, et al. J. Endocrinol. 154 (1997) 39–45.
(4) A. Vortkamp, et al. Mech. Dev. 71 (1998) 65–76,
(5) L. E. Freed, et al J. Biomed. Mater. Res. 27 (1993) 11–23.
(6) R. B. Pepinsky, et al. J. Biol. Chem. 273 (1998) 14037=14045.

EQUIVALENTS

Those skilled in the art will recognize, or be able to ascertain using no more than routine experimentation, many equivalents to the specific embodiments of the invention described herein. Such equivalents are intended to be encompassed by the following claims.

This application hereby incorporates by reference U.S. Provisional Application No. 60/200,767, Filed Apr. 28, 2000.

What is claim is:

1. A method of making a cartilaginous prosthesis, comprising seeding a polymeric matrix construct with chondrocytes and contacting the seeded construct with a hydrophobically modified hedgehog polypeptide which binds to patched and activates hedgehog signaling, which hedgehog polypeptide comprises a sequence of a naturally-occurring hedgehog polypeptide or N-terminal autoproteolytic fragment thereof, wherein the seeded construct is contacted with at least 500 ng/ml of said modified hedgehog polypeptide, and wherein said hydrophobically modified hedgehog polypeptide is modified with two palmitoyl moieties.

2. The method of claim 1, wherein the chondrocytes are articular chondrocytes.

3. The method of claim 1, wherein the hydrophobically modified hedgehog polypeptide is dipalmitoyl sonic hedgehog or dipalmitoyl indian hedgehog.

4. The method of claim 3, wherein the seeded construct is contacted with the dipalmitoyl hedgehog polypeptide at a concentration of at least 500 ng/ml.

5. The method of claim 4, wherein the seeded construct is contacted with the dipalmitoyl hedgehog polypeptide at a concentration of between 500 and 1000 ng/ml, and wherein the hedgehog polypeptide is a sonic hedgehog polypeptide.

6. The method of claim 1, wherein the polymeric matrix is selected from any of polyglycolid acid, collagen, dextran sulfate, polyanhydride, polyorthoester, hyaluronic acid-based polymers, and a glycosaminoglycan.

* * * * *